(12) United States Patent
Carter

(10) Patent No.: US 8,992,452 B2
(45) Date of Patent: Mar. 31, 2015

(54) LOAD CARRIER FRAME AND SYSTEM

(75) Inventor: Paul Carter, Fayetteville, NC (US)

(73) Assignee: Archangel Armor LLC, Fayetteville, NC (US)

( * ) Notice: Subject to any disclaimer, the term of this patent is extended or adjusted under 35 U.S.C. 154(b) by 8 days.

(21) Appl. No.: 13/272,682

(22) Filed: Oct. 13, 2011

(65) Prior Publication Data

US 2013/0261521 A1 Oct. 3, 2013

Related U.S. Application Data

(60) Provisional application No. 61/393,344, filed on Oct. 14, 2010.

(51) Int. Cl.
*A61F 5/00* (2006.01)
*A61F 5/02* (2006.01)

(52) U.S. Cl.
CPC ............... *A61F 5/028* (2013.01); *A61F 5/022* (2013.01)
USPC .............................................. 602/19; 602/5

(58) Field of Classification Search
CPC ........... A61F 5/024; A61F 5/026; A61F 5/28; A61F 5/0193; A61F 5/0585
USPC .................... 2/44, 45, 102; 602/5, 24, 17–19; 128/96.1, 99.1, 100.1, 101.1
See application file for complete search history.

(56) References Cited

U.S. PATENT DOCUMENTS

| | | | | |
|---|---|---|---|---|
| 1,174,757 | A | * | 3/1916 | Packer ............................ 602/19 |
| 4,976,257 | A | * | 12/1990 | Akin et al. ...................... 602/19 |
| 5,342,289 | A | * | 8/1994 | Munny ............................ 602/19 |
| 5,464,137 | A | * | 11/1995 | Shirdavani ..................... 224/265 |
| 8,556,840 | B2 | * | 10/2013 | Burke et al. .................... 602/19 |
| 2010/0076359 | A1 | * | 3/2010 | Glenn ............................ 602/19 |
| 2011/0105971 | A1 | * | 5/2011 | Ingimundarson et al. ...... 602/19 |
| 2011/0114101 | A1 | * | 5/2011 | Tweardy et al. .............. 128/870 |
| 2011/0152737 | A1 | * | 6/2011 | Burke et al. .................... 602/19 |
| 2012/0022420 | A1 | * | 1/2012 | Sandifer et al. ................ 602/19 |

* cited by examiner

*Primary Examiner* — Kim M Lewis

(57) ABSTRACT

Upper assembly including slot, hole array. Lower assembly conforming to hips. Lower assembly anchoring holes shaped/spaced as array. Lower assembly fastener hole for each slot; fastener hole having same position relative to anchoring holes as slot to array; having horizontal dimension equal to horizontal dimension of corresponding slot. Adjuster plate including anchoring points spaced as array holes. Each anchoring point dimensioned less than corresponding hole so as to fit snugly therein, and projecting a distance equal to thickness of corresponding upper and lower assembly anchoring hole. Forming an adjuster plate fastener hole for each lower assembly fastener hole. Each adjuster plate fastener hole having same position relative to anchoring points as slot to array. Releasable fastener for each lower assembly fastener hole. As assembled, fastener secures adjuster plate to upper and lower assembly such that anchoring points of adjuster plate are positioned through upper assembly and lower assembly anchoring holes.

5 Claims, 9 Drawing Sheets

500

LOAD CARRIER FRAME AND SYSTEM

CROSS-REFERENCE TO RELATED APPLICATION

This application is based upon and claims the benefit of U.S. Provisional Patent Application Ser. No. 61/393,344, filed on Oct. 14, 2010; the entire contents of which are incorporated herein by reference for all purposes.

FIELD

The technology disclosed herein (the "technology") relates to load carriers and systems thereof.

BRIEF DESCRIPTION OF THE DRAWINGS

Reference will now be made, by way of example, to the accompanying drawings which show example implementations of the present application.

DETAILED DESCRIPTION

Reference will now be made in detail to implementations of the technology. Each example is provided by way of explanation of the technology only, not as a limitation of the technology. It will be apparent to those skilled in the art that various modifications and variations can be made in the present technology without departing from the scope or spirit of the technology. For instance, features described as part of one implementation can be used on another implementation to yield a still further implementation. Thus, it is intended that the present technology cover such modifications and variations that come within the scope of the technology.

Referring to the figures, a core frame comprises an upper assembly, a lower assembly, and an adjuster plate. The upper assembly includes parts that align along the user's back and rise over the user's shoulders. This is one place that attachment points can be located and the padding can be located. The upper assembly is connected to the lower assembly. The lower assembly. The overlap between the upper and lower assemblies provides a region for adjusting the core frame. The lower assembly can fit around a user's hips; it is shaped like a "C" and sculpted in vertical profile slightly inward to fit over the top of the user's hips. Strapping and padding is applied over the core frame to make it more comfortable to the user and to provide increased support and better weight distribution. When padding and strapping are in place, the technology can substantially parallel the natural curvature of a user's spine—placing the spine closer to a neutral posture position. In some embodiments, the upper assembly and the lower assembly can be made of carbon fiber.

Figure 9:
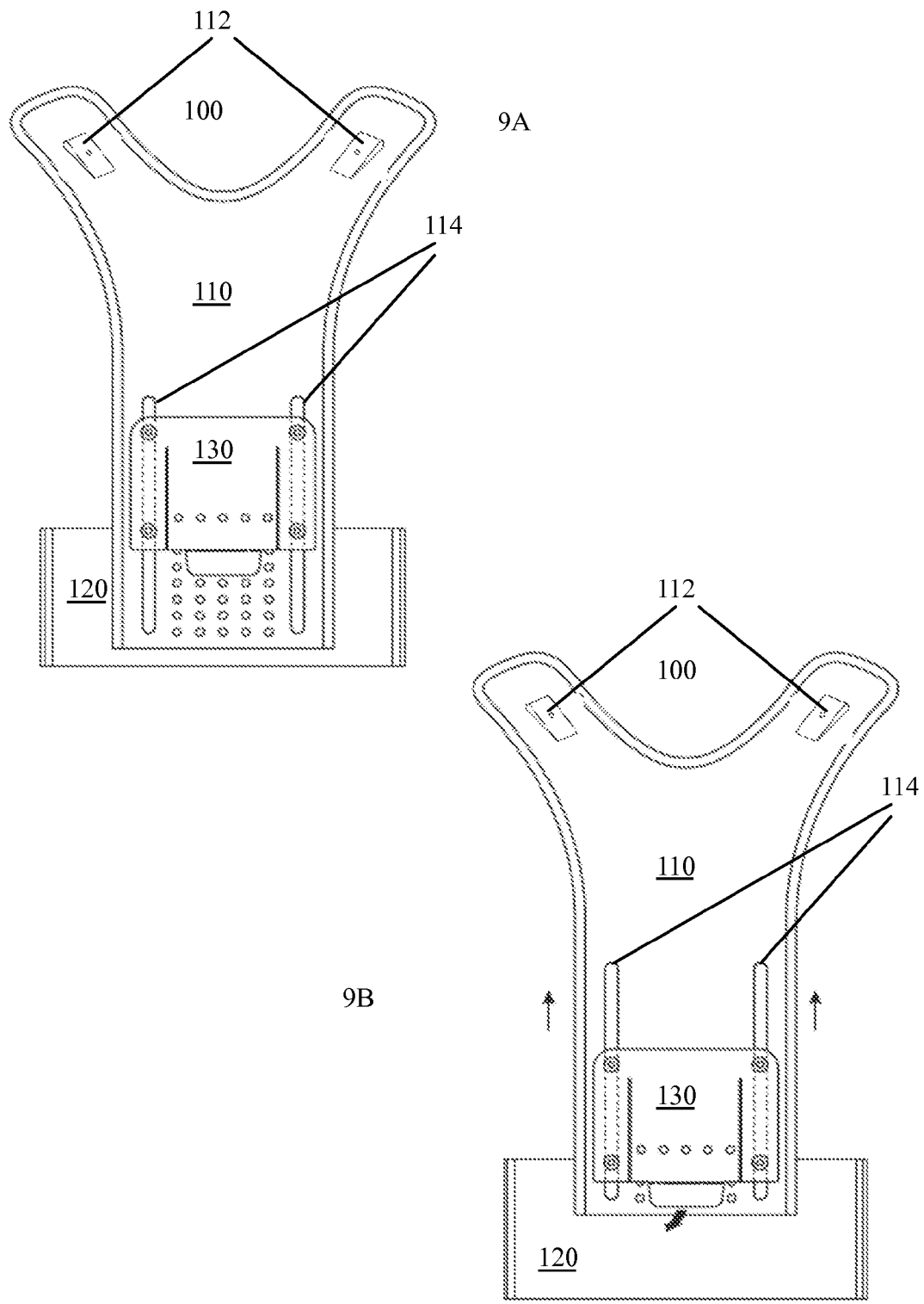
FIGS. 9A and B illustrate adjustment of the core frame.

The adjuster plate can be of a variety of materials such as spring steel. The adjuster plate can be substantially rectangular. As shown in the figures, each corner of the adjuster plate can have an attachment point (e.g. a hole) for connecting the adjuster plate to both the upper assembly and the lower assembly in an aligning fashion. A first of the assemblies (in the figures, the lower assembly) can have holes corresponding to those on the adjuster plate. A second of the assemblies (in the figures; the upper assembly) can have vertical slots of width substantially equal to the width of the holes in the adjuster plate and the first assembly, each slot aligned with two of the holes in the adjuster plate as shown in the figures. A fastener can be used in each of the holes to snugly adjust the overall height of the core frame, e.g., by sliding the second assembly relative to the first assembly and the adjuster plate and snugly fastening the adjuster plate fasteners, as shown in FIG. 9A (before adjusting) and FIG. 9B (after adjusting).

The adjuster plate can further include a series of posts (shown in the figures as a single horizontally-arranged array) that can mate with corresponding holes in a first assembly (in the figures, the lower assembly). The adjuster plate can include one or more posts in various configurations including a plurality of horizontal rows of differing numbers of posts. The first assembly is shown in the figures with a single row of holes corresponding to the posts of the adjuster plate of the figures. Posts can be canted down, can be circular, can be irregular polygons. The second assembly (the upper assembly in the figures) can include several array of holes, each array corresponding to the array of posts of the adjuster plate. In this fashion, the post can be fitted through the holes in the first assembly and adjustably fitted at various arrays in the second assembly to provide the user with a personalized vertical fit of the core frame. When the adjuster plate is made of resilient material, such as spring steel, the adjuster can be biased to have the posts engage the holes in the first and second assembly. A lip at the bottom (or top) of the adjuster plate can provide a convenient hand hold for temporarily countering the engagement bias for adjusting the core frame.

The adjustable support structure provided by the core frame can be used to support personal protective equipment (e.g., an armor carrier) and load carrying equipment while transferring weight to the user's hips for a wide variety of user sizes. Other mechanisms that can be used to secure the upper assembly to the lower assembly with an adjuster plate, including hook and loop, snaps, spring impelled posts, magnetically impelled posts, pneumatically impelled posts, webbing. In some embodiments, the securing mechanism can be integrated into the upper and lower assemblies and the adjuster plate can be dispensed with.

Attachment points on the core frame, e.g., two points at the top of the frame and two points at the bottom of the core frame, can be used to attach the various personal protective equipment and load carrying equipment to the core frame.

The lower assembly includes a hip belt portion that can wrap around a user's waist and hips. The hip belt portion of the lower assembly can be substantially rigid in the vertical direction and radially resilient. A flexible securable belt can be attached to the lower assembly (e.g., permanently or releasably), in a position to allow a user to secure the overall system substantially atop the user's hips. The belt can include attachment points (e.g., MOLLE) for the equipment of the type described above. A hip pad can be soft sewn and can slide over each of the ends of the hip belt (or in some embodiments, the belt regions of the lower assembly). The soft sewn portions of the hip belt can comprise as sandwich fold secured by hook and loop for various purposes such as to accommodate a ballistic panel, to be used as storage for excess webbing.

Removable lumbar padding assembly can be included in the technology. The lumbar padding assembly can be removably attached to the lumbar portion of the core frame. The attachment points can be the same corner fasteners used to secure the lower assembly to the adjuster plate. The lumbar padding assembly can accept various thicknesses and shapes of padding materials to conform the padding to the back of various users.

The upper yoke portion of the core frame upper assembly can be cut low at the base of a user's neck so as to reduce interference with user movement, e.g., when the user tilt's his head back. In the shoulder wing region of the upper assembly (e.g., the region corresponding to the middle of a user's shoulder blades), each side (lefty, right) of the upper assembly can include a wedge elevated towards the rear external portion, e.g., to allow routing of substantially rigid stays (e.g., aluminum) so that the stays protrude just over a user's shoulder to provide spacing that substantially prevents significant loading of the user's shoulders under heavy payloads. Through the wedge and through the upper portion of the lower back are anchoring points for securing the stays to the core frame (and in some embodiments for securing the harnessing).

Near the end of each shoulder wing, the upper assembly holes for further attachment points can be included for anchoring points for an adjustable shoulder strap that can run from the attachment point to the belt region of the lower assembly (e.g., attaching to that region of the lower assembly or to a covering or attachment point thereof). The shoulder strap can be straight from shoulder to hip or curved (e.g., in a radius about the shoulder and then to the hip). The strap can be padded. The strap can include a lateral stiffener, and can have webbing as a primary load bearing element. The webbing can be laterally contoured to the strap, e.g., by applying a plurality of substantially high tension thread lines on the inside radius of each curve. The entire webbing can be sewn flush to the strap. The strap can be secured to the core frame by various methods, e.g., a grommet through webbing at the top of the shoulder strap and using a rivet to attach.

A harness assembly can be included using a variety of materials to allow a user to hand carry the technology, or for others to extract, drag, or carry a user who is wearing the technology. The harness assembly can comprise a handle that would extend above the nape of the neck of a user, e.g., allowing a person to grab and drag a user wearing the technology. The harness can attach to the upper yoke at the same location as the stays, including extending from each upper yoke attachment point diagonally across the upper assembly in the direction of the lower assembly, e.g., both sides together forming an "X" across the back of the upper assembly, then the harness can be routed through the user's legs and be attached to the front hip portion of the technology. The attachment points at the hip can correspond to the hip attachment points of the shoulder straps, thus creating a body harness. A base of Kevlar coated with nomex having an outer coating to protect it from externals. Materials such as this provide a harness that is resistant to various environmental extremes, e.g., extreme heat from a fire.

The technology can include a variety of carriers, e.g., military ballistic carriers, aprons, protective apparel or equipment, occupational equipment, various tactical, medical equipment, including a military tactical carrier for carrying body armor.

When a cummerbund is used is can snug the user's body to the frame snugly. This encourages back posturing and position to go to neutral position. This can lessen loading on the spine.

Because the core frame provides support, some portions of conventional armor carriers can be omitted, e.g., stiffeners, padding, etc. The technology can provide an interface to existing armor carrier pieces, e.g., through the use of adapters.

Webbing on carriers of the technology provide attachment points for items such as collars, deltoid protection, lower back armor, and groin protection. The carriers are adapted for routing wiring for electronics such as a radio antenna. Such adaptations include ports in the fabric for routing wiring in a fashion protected from the elements. The carrier provides attachment points for quick-release mechanism.

Regarding stays, e.g., aluminum stays, attachment can be through adhesives, through molding the stays into elements of the core frame, through sets nuts, rivet screws. The stays can share a common lower attachment point, e.g., a depicted in the mid-back in the figures. Each stay then has an attachment point on the wedge in each upper assembly shoulder wing. This can provide separation, e.g., 1", from both the top of the wearer's shoulder and the front of the wearer's shoulder, thus allowing shoulder movement without substantial should restriction. The technology can include a pack system releaseably attachable to the core frame, with or without the armor carrier underneath. The pack can be truncated pear shaped to provide a truncated pear shape. The pack can be 10" across at the top, 14" across near the bottom and 12" at the bottom. The pack can be 6" deep at the top, 8" deep at the bottom, about 2000 cubic inches. The pack can be about 22" tall not counting addition 5" of collapsible collar that can be cinched tight to close the top of the bag. There can be three (3) points of access, top, and each of left and right side (using a zipper panel). The body can be of two-ply fabric or multiple fabrics (e.g., mil spec cloth on the outside and pack cloth on the inside with slick side facing inside—allowing routing of cables and other items between the layers using ports in the layers. The pack can be attached to the frame via a quick release system or other known attachment mechanisms, including permanent mounting. The pack can have one large inner chamber.

Figure 1:
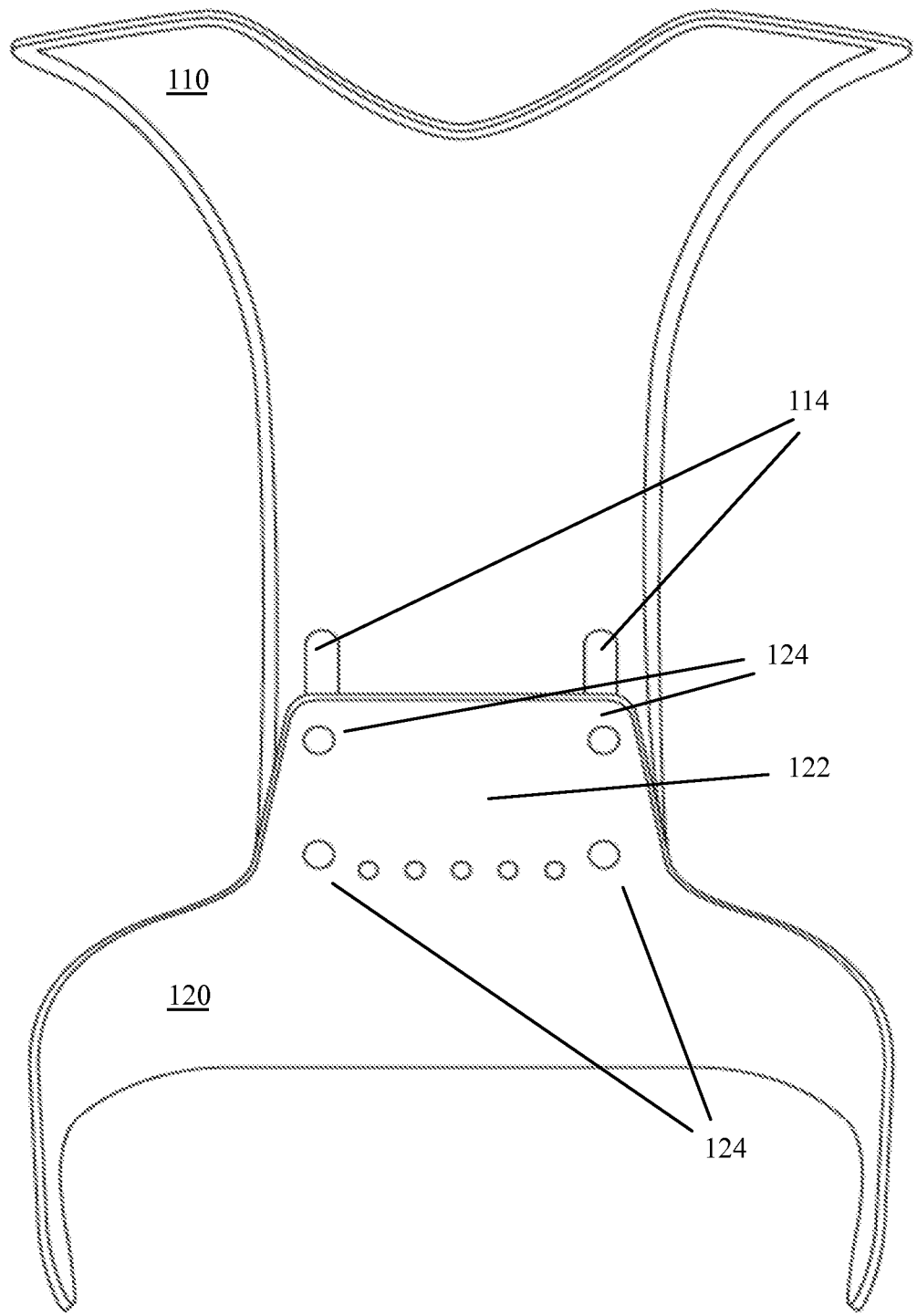
FIG. 1 illustrates a front view of an assembled core frame of some embodiments of the technology.
Figure 2:
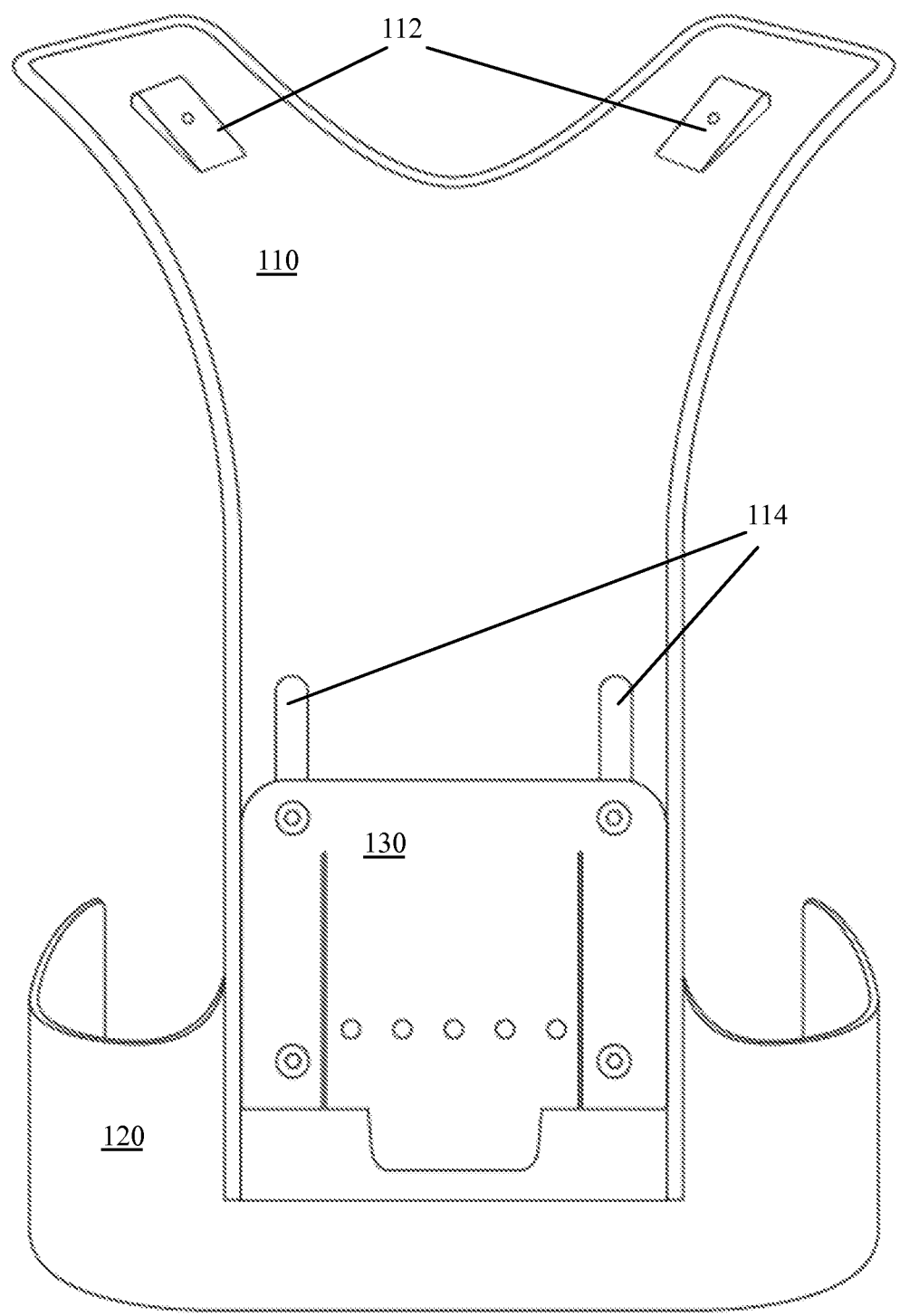
FIG. 2 illustrates a rear view of an assembled core frame of some embodiments of the technology.
Figure 3:
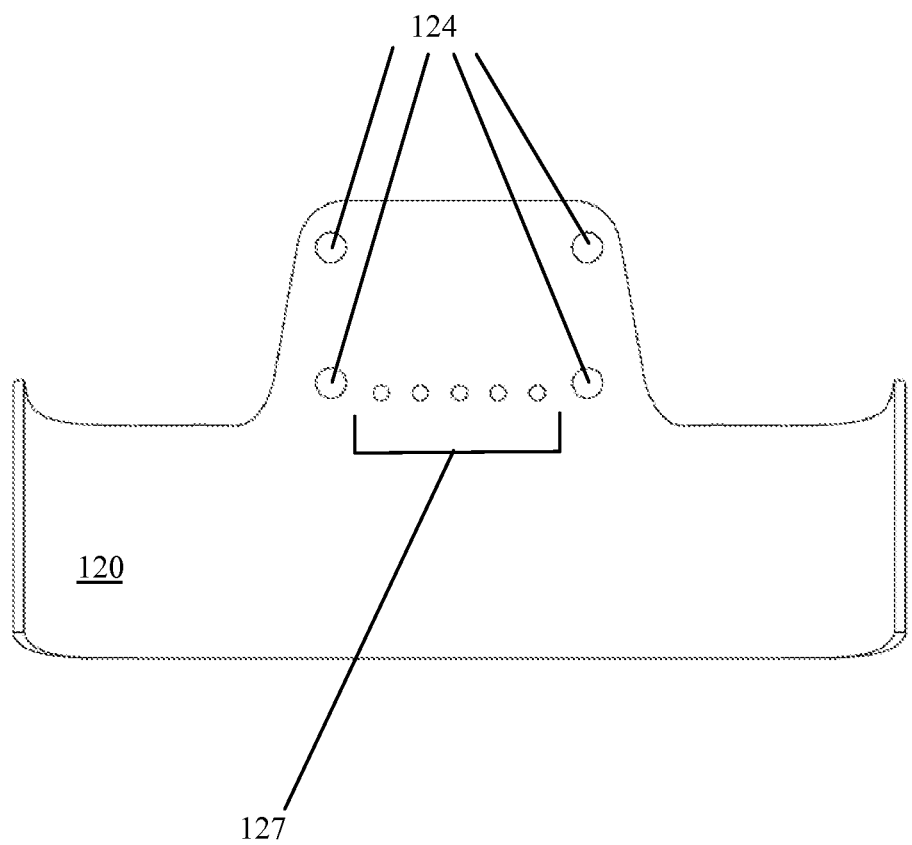
FIG. 3 illustrates a front view of a lower assembly of some embodiments of the technology.

Referring to FIG. 1, a front view of a core frame 100 of the present technology is illustrated—while in FIG. 2, a rear view of the core frame 100 is illustrated. The core frame 100 can include an upper assembly 110 releasably attachable to a lower assembly 120 using an adjuster plate 130 (not shown in FIG. 1).

Figure 4:
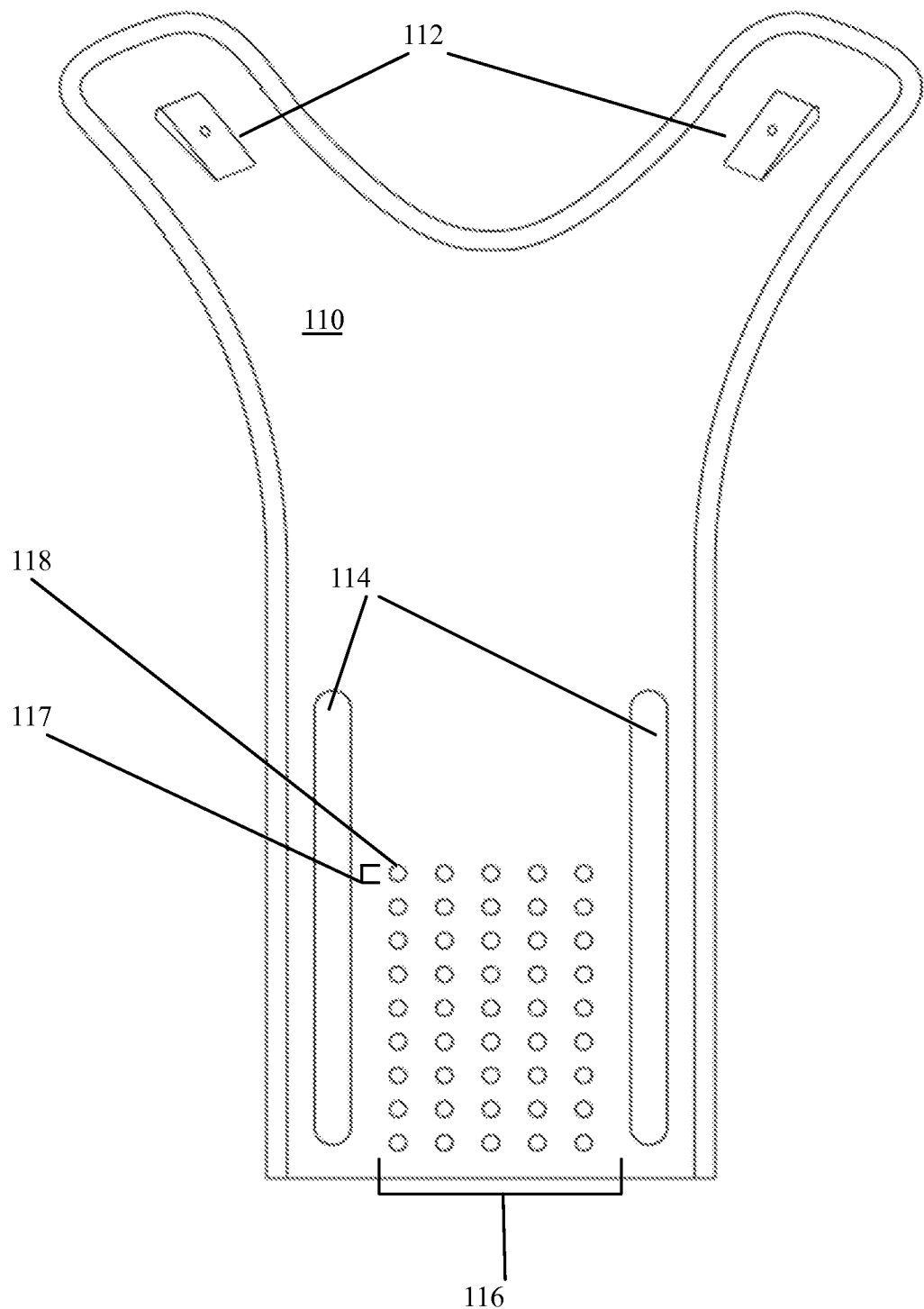
FIG. 4 illustrates a rear view of an upper assembly of some embodiments of the technology.
Figure 5:
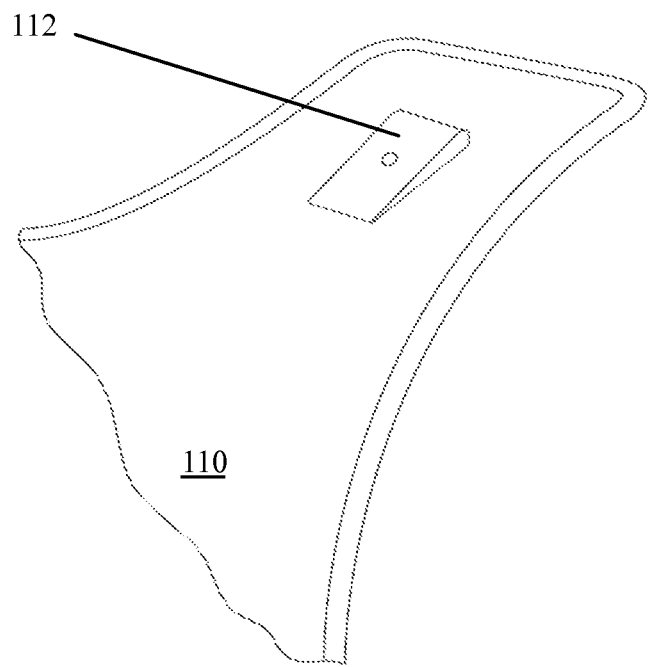
FIG. 5 illustrates a detail rear view of a shoulder wing portion of an upper assembly of some embodiments of the technology.
Figure 6:
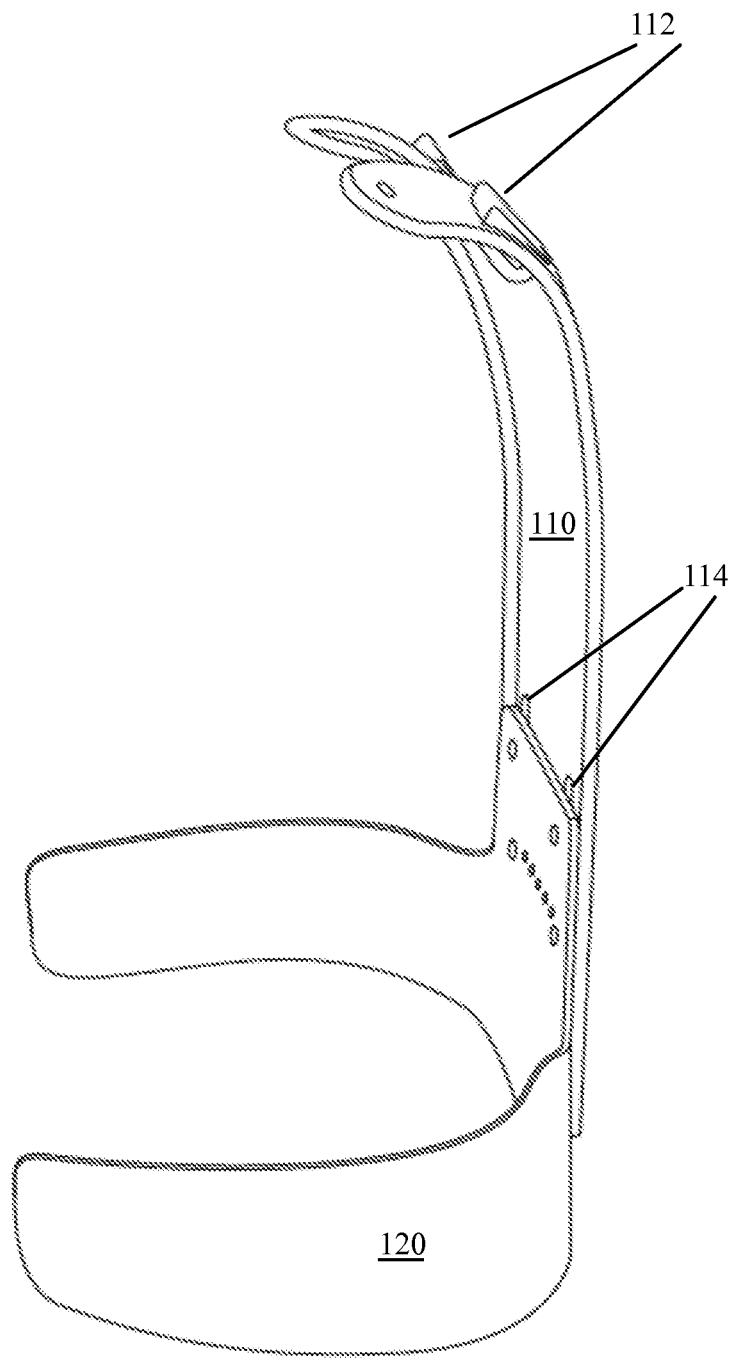
FIG. 6 illustrates a side views of a core frame of some embodiments of the technology.

As shown in FIG. 6 (left side perspective view), the upper assembly 110 formed substantially in the shape of a "Y," can be shaped to substantially mirror the natural thoracic curve of a user's spine. As illustrated in FIG. 4, a rear view of an upper assembly 110 is illustrated showing fastener slots 114 and a set 116 of rows 117 of anchor point mating holes 118. As illustrated in FIG. 2, FIG. 4, and FIG. 6, the upper assembly 110 includes two (2) wedges 112 for anchoring straps and/or stays.

As shown in FIG. 1 (front view), FIG. 2 (rear view), FIG. 6 (left side perspective view), lower assembly 120 can be shaped to substantially mirror the shape of a user's hips, with a mating section 122 for mating with the upper assembly 110 and the adjuster plate 130. Mating section 122 includes fastener holes 124 positioned to align with upper section fastener slots 114 and a row of lower assembly anchor point mating holes 127 positioned to align with a selectable one of the rows of upper assembly anchor point mating holes 117 in the assembled core frame 110.

Figure 7:
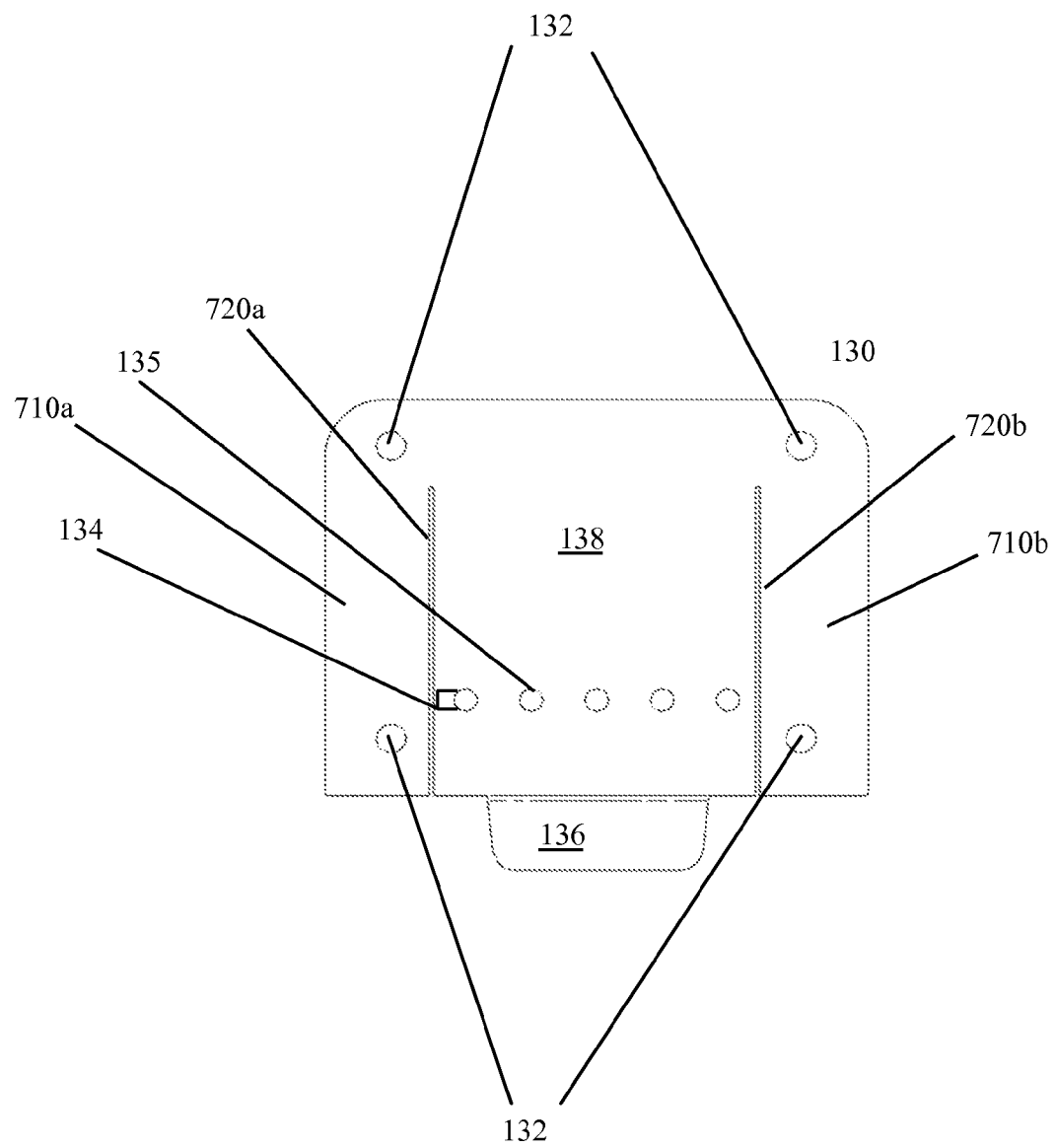
FIG. 7 illustrates a front view of an adjuster plate of some embodiments of the technology FIG. 8 illustrated a sectional side view of an adjuster plate, upper assembly, and lower assembly of some embodiments of the technology as assembled into a core frame.
Figure 8:
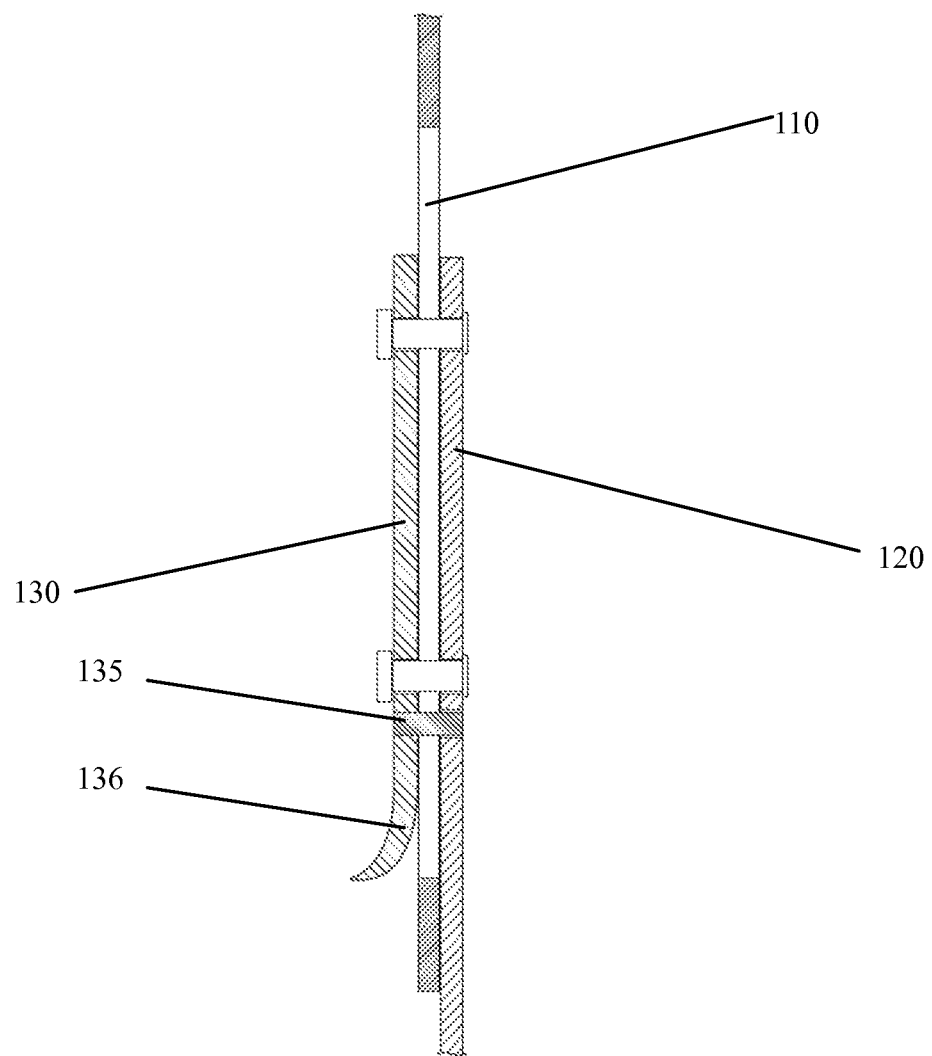

Adjuster plate 130, as illustrated in FIG. 2 and FIG. 7 can include a plurality of holes 132 for accepting releasable fasteners and at least one row 134 of anchoring points 135. Adjuster plate 130 can be attached to upper assembly 110 and lower assembly using releasable fasteners through fastener holes 132 in the adjuster plate 130, and through fastener slots 114 in the upper assembly 110, and through fastener holes 124 in the lower assembly. Each of the anchoring points 135 in the row 134 of anchoring points can be inserted through corresponding the holes of a row 117 of mating holes in the upper assembly 110. The particular row chosen will determine the height of the overall core frame. The adjuster plate anchoring points 135 can also penetrate the lower assembly mating holes 127. The entire assembly can be secured by securing fasteners through the fastener holes 124 and 132 and the fastener slots 114. Adjuster plate 130 can be fabricated from a biasable material, such as spring steel so that adjuster plate central portion 138 biases anchoring points 135 through the corresponding anchoring holes in upper portion 110 and lower portion 120. As shown in FIG. 8, adjuster plate central portion 138 is flanked by two wing portions, 710a and 710b, separated from adjuster plate central portion 138 by gap 720a and 720b respectively. Adjuster plate 130 can include a tail portion 136 to facilitate gripping of the adjuster plate to release the anchoring points 135 from holes 124 and 132 to adjust the overall height of the core frame 100.

The invention claimed is:

1. A load carrier:
comprising:
an upper assembly, forming therein: at least one substantially vertical slot, and an array of upper assembly anchoring holes;
a lower assembly:
shaped substantially to conform to a shape of a user's hips at least from one iliac crest of the user, around the user's back, to at least the other iliac crest of the user; and
forming therein, at an area corresponding approximately to the user's lower back:
a row of lower assembly anchoring holes, the holes within the row of lower assembly anchoring holes spaced substantially the same as the spacing of the holes of a row of the array, and each lower assembly hole substantially the same size and shape as a corresponding hole in a row of the array; and
at least one lower assembly fastener hole for each slot, each lower assembly fastener hole having: the same horizontal position relative to the row of lower assembly anchoring holes as the slot has to the array; and having a horizontal dimension substantially equal to the horizontal dimension of the corresponding slot;
an adjuster plate:
comprising a row of anchoring points spaced substantially the same as the spacing of holes of a row of the array, each anchoring point: having horizontal and vertical dimensions marginally less than the corresponding dimensions of a corresponding hole in a row of the array so as to fit snugly therein, and projecting a distance substantially equal to the combined thickness of the corresponding upper assembly anchoring hole and the lower assembly anchoring hole; and
forming therein at least one adjuster plate fastener hole for each lower assembly fastener hole, each adjuster plate fastener hole having: the same horizontal position relative to the row of anchoring points as the slot has to the array, and dimensions substantially equal to the size and shape of the corresponding lower assembly fastener hole; and
one releasable fastener for each fastener hole formed in the lower assembly; and
wherein, in an assembled configuration of the load carrier, the at least one releasable fastener secures the adjuster plate to the upper assembly and the lower assembly such that the anchoring points of the adjuster plate are positioned through the upper assembly anchoring holes, and then through the lower assembly anchoring holes.

2. The load carrier of claim 1, wherein the upper assembly is shaped substantially in the form of the thoracic curve of a user's spine.

3. The load carrier of claim 1:
wherein the adjuster plate further comprises a central portion comprising the anchoring points, the central portion biased in a direction of the projection of the anchoring points; and two wing portions, one to each side of the central portion, among which each adjuster plate fastener hole is formed;
wherein the central portion is separated from the wing portions by a gap from a point above the row of anchoring points to the bottom of the adjuster plate.

4. The load carrier of claim 3, wherein the fasteners allow sliding engagement along a major axis of the slot a configuration of the assembly where the anchoring points are disengaged from the lower portion anchoring holes and the upper portion anchoring holes against a bias of the adjuster plate central portion.

5. The load carrier of claim 1:
wherein the upper portion is formed substantially in the shape of a "Y," and the upper portion further comprises, on each arm of the "Y," a wedge having a substantially downward facing apex.

* * * * *